US010722669B2

(12) United States Patent
Reed

(10) Patent No.: US 10,722,669 B2
(45) Date of Patent: *Jul. 28, 2020

(54) COMBINATION ENHANCED THERAPY

(71) Applicant: ResMed Pty Ltd, Bella Vista, New South Wales (AU)

(72) Inventor: Nicholas Jerome Reed, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 731 days.

This patent is subject to a terminal disclaimer.

(21) Appl. No.: 15/393,058

(22) Filed: Dec. 28, 2016

(65) Prior Publication Data

US 2017/0106158 A1    Apr. 20, 2017

Related U.S. Application Data

(63) Continuation of application No. 14/148,055, filed on Jan. 6, 2014, now Pat. No. 9,566,403, which is a
(Continued)

(51) Int. Cl.
*A61M 16/06* (2006.01)
*A61M 16/00* (2006.01)
*A61M 16/08* (2006.01)

(52) U.S. Cl.
CPC ...... *A61M 16/0066* (2013.01); *A61M 16/021* (2017.08); *A61M 16/06* (2013.01);
(Continued)

(58) Field of Classification Search
CPC .............. A61M 16/00; A61M 16/0051; A61M 16/0057; A61M 16/0063; A61M 16/0066;
(Continued)

(56) References Cited

U.S. PATENT DOCUMENTS 4,323,064 A    4/1982    Hoenig
4,340,044 A    7/1982    Levy
(Continued)

FOREIGN PATENT DOCUMENTS

CN    1440302    9/2003
WO    2001/32069    5/2001
(Continued)

OTHER PUBLICATIONS

Chinese Notification of the Second Office Action and its partial English translation for corresponding Chinese Application No. 201510347413.1, dated Apr. 2, 2018 (10 pages).
(Continued)

*Primary Examiner* — Annette Dixon
(74) *Attorney, Agent, or Firm* — Nixon & Vanderhye, P.C.

(57) ABSTRACT

A Positive Airway Pressure (PAP) device includes a flow generator that generates a supply of pressurized air. The flow generator includes a programmable controller. The programmable controller is adapted to allow continuous access to at least one active operating mode and selective access to at least one dormant operating mode. The programmable controller includes a mode control system adapted to receive a data signal to control the selective access to the at least one dormant operating mode.

20 Claims, 2 Drawing Sheets

Related U.S. Application Data continuation of application No. 11/707,160, filed on Feb. 16, 2007, now Pat. No. 8,640,697.

(60) Provisional application No. 60/774,222, filed on Feb. 17, 2006.

(52) U.S. Cl.
CPC ..... *A61M 16/0875* (2013.01); *A61M 2205/27* (2013.01); *A61M 2205/3569* (2013.01); *A61M 2205/3584* (2013.01); *A61M 2205/3592* (2013.01); *A61M 2205/502* (2013.01)

(58) Field of Classification Search
CPC .......... A61M 16/0069; A61M 16/0072; A61M 16/0075; A61M 16/024; A61M 16/04; A61M 16/042; A61M 16/0465; A61M 16/06; A61M 16/101; A61M 16/107; A61M 16/12; A61M 16/16; A61M 16/204; A61M 2016/0021; A61M 2016/0027; A61M 2016/0039; A61M 2016/0042; A61M 2016/1025; A61M 2202/0275; A61M 2205/16; A61M 2205/276; A61M 2205/3365; A61M 2205/3368; A61M 2205/3375; A61M 2205/3553; A61M 2205/3561; A61M 2205/3569; A61M 2205/3584; A61M 2205/3592; A61M 2205/42; A61M 2205/50; A61M 2205/502; A61M 2205/505; A61M 2205/52; A61M 2205/8206; A61M 2210/0618; A61M 2230/005; A61M 2230/08; A61M 2230/432; A61M 2230/435; A61M 2230/60; A61M 2230/63; F04D 17/164; F04D 29/282; F04D 29/442

See application file for complete search history.

(56) References Cited

U.S. PATENT DOCUMENTS

| | | | |
|---|---|---|---|
| 4,944,310 A | 7/1990 | Sullivan et al. | |
| 5,192,042 A | 3/1993 | Wotring et al. | |
| 5,199,424 A | 4/1993 | Sullivan et al. | |
| 5,241,592 A | 8/1993 | Carlson et al. | |
| 5,503,146 A | 4/1996 | Froehlich et al. | |
| 5,522,382 A | 6/1996 | Sullivan et al. | |
| 5,535,738 A | 7/1996 | Estes et al. | |
| 5,551,419 A | 9/1996 | Froehlich et al. | |
| 5,560,353 A | 10/1996 | Willemot et al. | |
| 5,598,838 A * | 2/1997 | Servidio | A61M 16/00 128/204.21 |
| 5,615,109 A | 3/1997 | Eder | |
| 5,692,497 A * | 12/1997 | Schnitzer | A61M 16/0051 128/204.21 |
| 5,704,345 A | 1/1998 | Berthon-Jones | |
| 5,794,625 A | 8/1998 | McCarley et al. | |
| 5,823,651 A | 10/1998 | Helot et al. | |
| 5,881,723 A | 3/1999 | Wallace et al. | |
| 6,000,608 A | 12/1999 | Dorf | |
| 6,029,665 A | 2/2000 | Berthon-Jones | |
| 6,105,575 A | 8/2000 | Estes et al. | |
| 6,138,675 A | 10/2000 | Berthon-Jones | |
| 6,158,433 A | 12/2000 | Ong et al. | |
| 6,349,724 B1 | 2/2002 | Burton et al. | |
| 6,363,933 B1 | 4/2002 | Berthon-Jones | |
| 6,543,449 B1 * | 4/2003 | Woodring | A61M 16/0051 128/204.18 |
| 6,609,517 B1 | 8/2003 | Estes et al. | |
| 6,705,315 B2 | 3/2004 | Sullivan et al. | |
| 6,886,948 B2 | 5/2005 | Nakano | |
| 6,983,126 B1 | 1/2006 | Saalman | |
| 7,128,069 B2 | 10/2006 | Farrugia et al. | |
| 7,188,621 B2 | 3/2007 | DeVries et al. | |
| 7,191,780 B2 | 3/2007 | Faram | |
| 7,225,809 B1 * | 6/2007 | Bowen | A61M 16/024 128/204.21 |
| 7,469,698 B1 * | 12/2008 | Childers | A61M 16/00 128/204.18 |
| 7,588,031 B2 | 9/2009 | Truschel et al. | |
| 7,779,834 B2 | 8/2010 | Calluaud et al. | |
| 7,913,689 B2 * | 3/2011 | Henry | A61M 16/00 128/204.21 |
| 7,942,823 B2 | 5/2011 | Wright et al. | |
| 7,958,892 B2 | 6/2011 | Kwok et al. | |
| 8,172,766 B1 | 5/2012 | Kayyali et al. | |
| 8,499,761 B2 | 8/2013 | Jorczak et al. | |
| 8,640,697 B2 * | 2/2014 | Reed | A61M 16/0066 128/204.21 |
| 9,566,403 B2 * | 2/2017 | Reed | A61M 16/0066 |
| 10,279,134 B2 * | 5/2019 | Kwok | A61M 16/0066 |
| 2003/0066529 A1 | 4/2003 | Truschel et al. | |
| 2003/0213489 A1 | 11/2003 | Mechlenburg et al. | |
| 2004/0054587 A1 | 3/2004 | Dev et al. | |
| 2004/0074496 A1 | 4/2004 | Hayashi et al. | |
| 2005/0061318 A1 | 3/2005 | Faram | |
| 2005/0178384 A1 | 8/2005 | Martin et al. | |
| 2005/0211761 A1 | 9/2005 | Antilla et al. | |
| 2006/0084877 A1 | 4/2006 | Ujhazy et al. | |
| 2006/0112959 A1 | 6/2006 | Mechlenburg et al. | |
| 2006/0124128 A1 | 6/2006 | Deane et al. | |
| 2006/0130836 A1 | 6/2006 | Wixey et al. | |
| 2006/0237014 A1 | 10/2006 | Makinson et al. | |
| 2007/0023045 A1 | 2/2007 | Kwok et al. | |
| 2007/0193583 A1 | 8/2007 | Reed | |
| 2007/0287895 A1 | 12/2007 | Brown | |
| 2010/0114218 A1 | 5/2010 | Heath | |
| 2010/0147301 A1 | 6/2010 | Kwok | |
| 2010/0236552 A1 | 9/2010 | Kwok et al. | |
| 2011/0192400 A9 | 8/2011 | Burton et al. | |
| 2011/0240024 A1 | 10/2011 | Kwok et al. | |
| 2014/0116438 A1 | 5/2014 | Reed | |
| 2018/0353716 A1 * | 12/2018 | Oates | A61M 16/024 |

FOREIGN PATENT DOCUMENTS

| | | |
|---|---|---|
| WO | 2002/002169 | 1/2002 |
| WO | 2002/018002 | 3/2002 |
| WO | 2003/024335 | 3/2003 |
| WO | 2004/067070 | 8/2004 |
| WO | 2004/112680 A2 | 12/2004 |
| WO | 2005/002655 A1 | 1/2005 |
| WO | 2005/028009 | 3/2005 |
| WO | 2005/063323 | 7/2005 |
| WO | 2005/065757 | 7/2005 |
| WO | 2005/077447 A1 | 8/2005 |
| WO | 2005/099798 | 10/2005 |

OTHER PUBLICATIONS

Chinese Notification of the First Office Action and its partial English translation for corresponding Chinese Application No. 201510347413.1, dated Feb. 22, 2017 (20 pages).
U.S. Appl. No. 60/624,951, filed Nov. 2004, Kwok et al.
U.S. Appl. No. 60/625,878, filed Nov. 2004, Kwok et al.
U.S. Appl. No. 60/656,880, filed Mar. 2005, Kwok et al.
U.S. Appl. No. 60/707,950, filed Aug. 2005, Kwok et al.
Chinese Decision of Rejection and its English translation for Chinese Application No. 201310228831X, dated Sep. 30, 2016 (16 pages).
Decision on Reexamination dated Mar. 18, 2015 in Chinese Application No. 200710087962.5, with English Translation (22pages).
Notification of Reexamination dated Dec. 26, 2014 in Chinese Application No. 200710087962.5, with English Translation (18 pages).
Notification of the First Office Action dated Jan. 7, 2015 in Chinese Application No. 201310228831.X, with English Translation (14 pages).

(56) References Cited

OTHER PUBLICATIONS

Notification of the Second Office Action dated Sep. 16, 2015 in Chinese Application No. 201310228831.X, with English Translation (9 pages).
Notification of the Third Office Action dated Apr. 1, 2016 issued in Chinese Application No. 201310228831.X with English translation (21 pages).
Office Action for U.S. Appl. No. 14/148,055, dated Feb. 29, 2016, 18 pages.
Office Action for U.S. Appl. No. 14/148,055, dated Jun. 22, 2016, 10 pages.
Office Action for U.S. Appl. No. 13/067,081, dated Aug. 11, 2014 (7 pages).
Office Action for U.S. Appl. No. 13/067,081, dated Jan. 5, 2015 (6 pages).
Office Action for U.S. Appl. No. 13/067,081, dated Feb. 4, 2015 (7 pages).
Office Action for U.S. Appl. No. 13/067,081, dated Jun. 23, 2015 (8 pages).
Office Action for U.S. Appl. No. 13/067,081, dated Oct. 2, 2015 (7 pages).
Office Action for U.S. Appl. No. 13/067,081, dated Mar. 10, 2016 (8 pages).
Office Action dated Mar. 31, 2012 in corresponding Chinese Application No. 200710087962.5 (with translation).
Office Action dated Aug. 30, 2011 in corresponding Chinese Application No. 200710087962.5 (with translation).
Office Action dated May 5, 2011 in corresponding Chinese Application No. 200710087962.5 (with translation).
Office Action dated Oct. 12, 2010 in corresponding Chinese Application No. 200710087962.5 (with translation).
U.S. Appl. No. 60/505,718, filed Sep. 25, 2003.
U.S. Appl. No. 11/707,160, filed Feb. 16, 2007.
Office Action dated May 17, 2019, issued in U.S. Appl. No. 15/179,381, 16 pages.
Decision of Rejection dated Nov. 30, 2018, issued in Chinese Application No. 201510347413.1 and English translation, 16 pages.
U.S. Appl. No. 60/703,457, filed Jul. 29, 2005.

\* cited by examiner

COMBINATION ENHANCED THERAPY

CROSS-REFERENCE TO RELATED APPLICATIONS

This application is a continuation of U.S. application Ser. No. 14/148,055, filed Jan. 6, 2014, now U.S. Pat. No. 9,566,403; which is a continuation of U.S. application Ser. No. 11/707,160, filed on Feb. 16, 2007, now U.S. Pat. No. 8,640,697, which claims the benefit of U.S. Provisional Application No. 60/774,222, filed Feb. 17, 2006, which is incorporated herein by reference in its entirety.

FIELD OF THE INVENTION

The present invention relates to a Positive Airway Pressure (PAP) device for ventilatory assistance and, more particularly, to a PAP device that provides at least one operating mode present in a dormant state.

BACKGROUND OF THE INVENTION

A Positive Airway Pressure (PAP) device is used in the treatment of sleep related breathing disorders such as Obstructive Sleep Apnea (OSA). Colin Sullivan was the first to invent the use of nasal Continuous Positive Airway Pressure (CPAP) to treat Obstructive Sleep Apnea (OSA), e.g., see U.S. Pat. No. 4,944,310. OSA is characterized by partial or complete occlusion (i.e., apnea) of the upper airway passage during sleep. OSA sufferers repeatedly choke on their tongue and soft palate throughout the entire sleep period resulting in lowered arterial blood oxygen levels and poor quality of sleep.

CPAP treatment generally provides a supply of air or breathable gas from a blower to a patient via an air delivery conduit and a patient interface, such as a full-face or nasal mask or nasal prongs. The air or breathable gas is commonly delivered at a pressure of 4 cmH$_2$O to 28 cmH$_2$O and acts as a splint to hold the airway open during sleep. CPAP therapy has been shown to effectively eliminate both snoring and obstructive sleep apneas. However, some patients complain of discomfort with CPAP therapy.

The pressure required for effective CPAP therapy differs between patients. In order to determine an individual's effective CPAP therapy pressure, the individual generally undergoes a sleep study in a hospital, clinic or sleep laboratory. A complete sleep study commonly occurs over two nights, with diagnosis of OSA occurring the first night and pressure titration occurring the second night. On the first night, the individual is observed while asleep and parameters such as oxygen saturation, chest wall and abdominal movement, air flow, expired CO$_2$, ECG, EEG, EMG and eye movement are recorded. On the second night, the individual is provided with nasal PAP therapy and the delivered treatment pressure is altered in response to the presence of snoring or apneas. The minimum pressure required during the night to eliminate the snoring and apneas is determined to be the effective PAP therapy pressure.

Because breathing against a pressure elevated above ambient pressure can be uncomfortable, especially when trying to sleep, it is desirable to keep the PAP pressure as low as practicable, particularly if the individual requires long term treatment. Lower PAP pressures also result in a lower mask contact pressure which is generally more comfortable for the user. Thus, during PAP therapy it is desirable to use the lowest practicable treatment pressure that is effective in preventing occlusion in order to provide the higher levels of comfort and thereby promote compliance with treatment.

Another type of CPAP device known as a Bilevel CPAP device provides a first pressure during inhalation (commonly termed an IPAP) and a second, lower pressure during exhalation (commonly termed an EPAP). Some patients perceive that the lower pressure during exhalation is more comfortable, at least while they are awake. Examples of these devices include the ResMed VPAP® series, and the Respironics BiPAP® series. Bilevel CPAP devices may be prescribed for patients who are not compliant with single pressure CPAP devices.

A further type of CPAP mode designed to enhance patient comfort and compliance provides a rapid decrease in pressure at the beginning of expiration and then quickly returns to therapeutic pressure at or near the end of expiration. These algorithms are designed to overcome the perceived problem of exhaling against a high pressure and are termed Expiratory Pressure Relief (EPR) modes. This mode forms the basis of Respironics C-Flex mode. See published applications WO 2005/065757 and WO 2004/112680 and U.S. Pat. Nos. 5,535,738; 5,794,625; 6,105,575; 6,609,517 and 7,128,069.

Another way of improving patient comfort and compliance is to start each therapy session at a low therapeutic pressure (e.g., 4 cmH$_2$O), and then ramp up to full therapeutic pressure over a period of time such as the first hour. This allows the patient to adjust to the sensation while falling asleep. Alternatively, the device may be set to implement a time delay before full therapeutic pressure is applied, which allows the patient time to fall asleep before full therapeutic pressure is applied. See U.S. Pat. Nos. 5,199,424 and 5,522,382.

Another form of CPAP therapy can be provided by an automatically adjusting CPAP device such as the ResMed AUTOSET™ SPIRIT™ device. In this device, the CPAP pressure is automatically increased or decreased in accordance with indications of flow limitation, such as flow flattening, snore, apnea and hypopnea. See U.S. Pat. Nos. 5,704,345; 6,029,665; 6,138,675; and 6,363,933. These patents also describe a method and apparatus for distinguishing between so-called "central" and obstructive apneas. More recently, automatically adjusting Bilevel devices have been described where both the IPAP and the EPAP pressures are capable of being automatically increased or decreased in accordance with indications of flow limitation as described above. See pending patent application WO 2005/063323.

An advantage of an automatically adjusting system is that it provides the patient with an elevated PAP only when required. This means that the patient is spared the discomfort of receiving the highest treatment pressure during the whole treatment session. Furthermore, while the treatment pressure required for a particular patient may vary over time, a correctly functioning automatic system can obviate the need for the patient to return for a subsequent sleep study to reset the treatment pressure delivered by the PAP device.

Generally, PAP devices are made and tested to work most efficiently with particular patient interface systems. However, the PAP devices and patient interface systems are sold as separate components of the therapy equipment. Thus, patients may decide to use a particular PAP device together with a patient interface system that was not specifically tested for that PAP device. This may result in a less than efficient therapy system. Therefore, a system that encourages consumers to buy compatible products may provide more efficient and/or comfortable therapy. Once compatible products are combined, they may deliver enhanced therapy benefits compared to the separate products alone.

The contents of all of the aforesaid patents are incorporated herein by cross-reference.

The present invention provides improvements to known PAP devices to enhance and/or facilitate the treatment session.

SUMMARY OF THE INVENTION

An aspect of the present invention is to provide a Positive Airway Pressure (PAP) device including a flow generator that generates a supply of pressurized air. The flow generator includes a programmable controller. The programmable controller is adapted to allow continuous access to at least one active operating mode and selective access to at least one dormant operating mode. The controller includes a mode control system adapted to receive a data signal to control the selective access to the at least one dormant operating mode.

Another aspect of the invention is to provide a patient interface system adapted to generate or otherwise provide a data signal that is adapted to activate a dormant operating mode present within a PAP device. For example, the data signal may be generated by or obtained from a proximity switch present in a patient interface connector or a radio frequency identification (RFID) tag present on the patient interface system.

A further aspect of the invention is to provide an electronic chip or card including a data signal that is adapted to activate a dormant operating mode present within a PAP device. The electronic chip or electronic card is adapted to communicate with the mode control system present in the PAP device.

The PAP device may further include at least one continuously available active operating mode. In an embodiment, the continuously available active operating mode is a Continuous Positive Airway Pressure (CPAP) mode.

The at least one dormant operating mode that is activated by a data signal may include any known PAP mode, e.g., an auto-adjusting pressure mode and/or an Expiratory Pressure Relief (EPR) mode.

Alternatively, the data signal may include a pin or code number that is inserted into the device using a user input unit, such as a keypad. In an embodiment, the pin or code number is input into the device via a telephone or Internet connection. The pin or code number may comprise numbers, letters and/or symbols or any combination thereof.

In an embodiment the dormant operating mode is activated for a predetermined time period. The predetermined time period is controlled by a clock that is activated by the data signal. The clock may count down or up a predetermined amount of time. The clock may count in real-time or the clock may count the patient compliance or device usage time such as hours of usage.

The dormant operating mode may be capable of repeated activation by obtaining new data signals.

Yet another aspect of the invention relates to a method for configuring a PAP device. The method includes programming the PAP device with at least one primary therapy delivery mode and at least one restricted-access dormant therapy delivery mode, and enabling access to the at least one dormant therapy delivery mode only upon receipt of an activation signal, command, and/or code.

Still another aspect of the invention relates to a method for encouraging the purchase of a PAP device and a peripheral component from a common supplier. The method includes programming the PAP device from the common supplier to operate in at least one primary therapy delivery mode and at least one restricted-access dormant therapy delivery mode that can be activated only upon receipt of an activation signal, code, or command, and enabling operation of the PAP device in the at least one dormant therapy delivery mode upon operative connection with the peripheral component from the common supplier that is associated with the activation signal, code, or command.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

1.1 PAP Device

Figure 1:
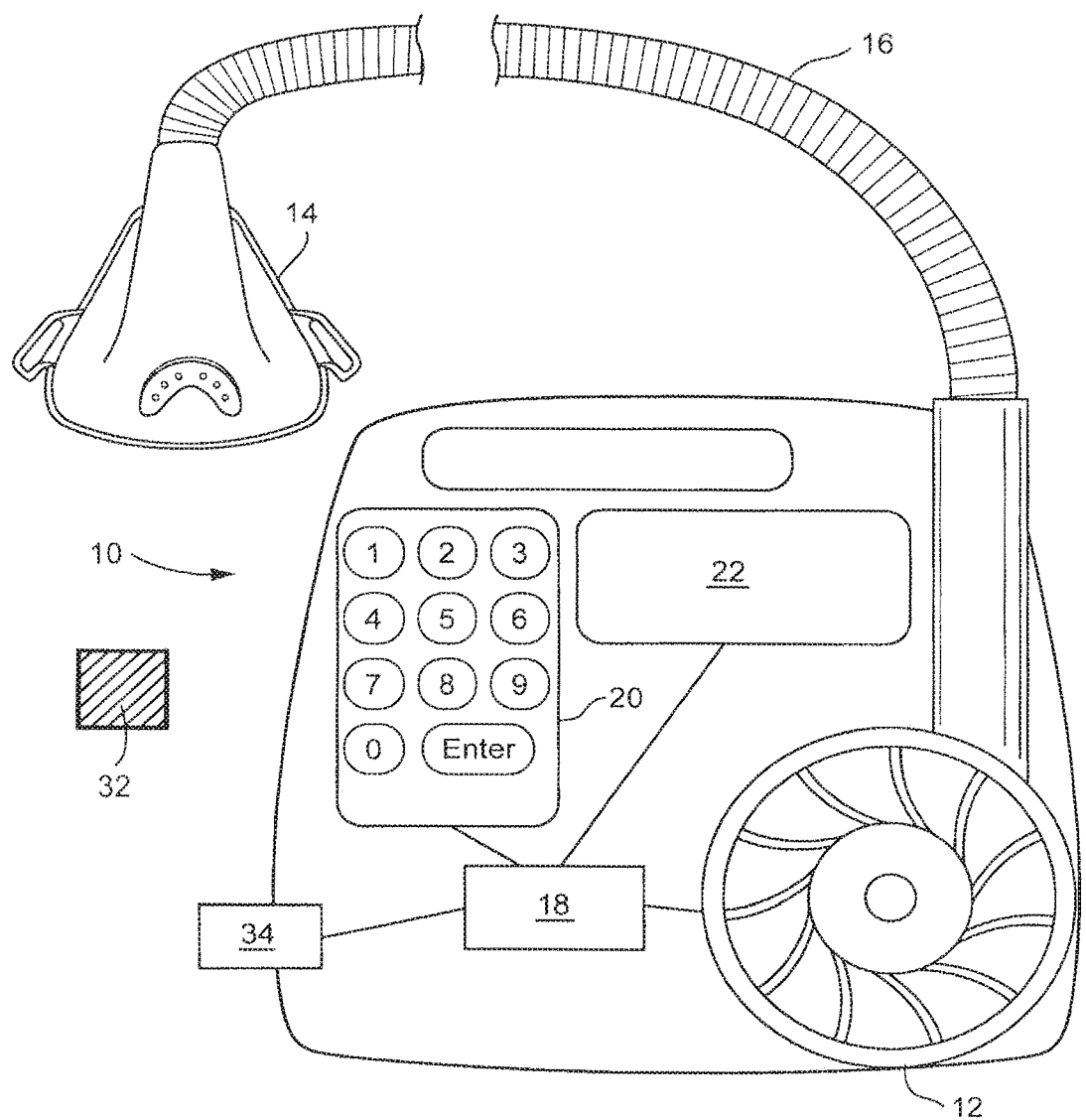
FIG. 1 is a perspective view of a flow generator system according to an embodiment of the invention.

FIG. 1 illustrates a PAP device 10, which is a type of a flow generator system, according to an embodiment of the present invention. As illustrated, the PAP device 10 includes a flow generator having a motor-driven impeller 12 that provides a supply of pressurized air for the administration of CPAP treatment. The pressurized air is delivered to a patient via a patient interface 14. An air delivery conduit 16 is coupled between the PAP device 10 and the patient interface 14. A programmable controller 18 controls the operations of the flow generator. The PAP device 10 may comprise a user interface unit 20 (e.g., a user input unit) to allow information input and a display unit 22 to display output information.

In an embodiment, the PAP device 10 includes at least two operating modes programmed into the programmable controller 18 at the time of manufacture. A first operating mode, termed the active operating mode, would be continuously available for use. The active operating mode may be a basic operating mode such as CPAP pressure mode, which delivers pressurized gas at a constant set pressure. A second operating mode, termed the dormant operating mode, would be present in the device in an inactive or dormant state such that the second operating mode is not freely available for use. The dormant operating mode would require activation from a data signal. The data signal would provide an activation signal to a mode control system 34 that is in communication with the programmable controller 18 and would enable operation of the dormant operating mode. The PAP device 10 may provide more than two operating modes with one or more operating modes being continuously available and one or more dormant operating modes requiring activation.

1.2 Patient Interface System

The patient interface 14 may have any suitable configuration as is known in the art, e.g., full-face mask, nasal mask, oro-nasal mask, mouth mask, nasal prongs, etc. Aspects of the invention may be used with both vented and non-vented masks and single or dual tube breathing gas supply systems.

1.3 Data Signal

The data signal 32 is capable of sending a signal to the mode control system 34 to enable activation of a dormant operation mode present within the PAP device 10. The mode control system 34 provides the access signal to activate a dormant operating mode present within the PAP device 10. The data signal 32 may be delivered to the mode control system 34 in the PAP device 10 using any appropriate device or system.

For example, in one embodiment, the data signal 32 may be carried by an electronic card or chip that is inserted into the PAP device 10 to provide the data signal 32 to the mode control system 34. In another embodiment, the dormant operating mode may be activated by inputting a specific pin number into the PAP device 10. The pin number would provide the data signal 32 to the mode control system 34 to subsequently activate the at least one dormant operating mode. The pin number may be input into the device 10 via the user interface unit 20 (e.g., a user input unit) or the pin number may be obtained or input into the device via a telecommunications connection such as a telephone line or the Internet. This later option may assist in preventing multiple machines from using the same pin number to activate the dormant operating mode by maintaining a record of pin numbers used and preventing further use. In an embodiment, the mode control system 34 may destructively read the data signal 32 to prevent repeated use of the data signal 32 to activate multiple devices.

In an alternative embodiment, the data signal 32 may be incorporated into a patient interface system. The connection of the patient interface system, including the air delivery conduit 16, to the PAP device 10 would provide the data signal 32 to the mode control system 34 to activate the at least one dormant operating mode. For example, the patient interface system and PAP device 10 may comprise proximity switches (e.g., magnetic reed switches), such as those described in ResMed's U.S. provisional application No. 60/707,950 to Kwok et al. filed 15 Aug. 2005, the entirety incorporated herein by reference. The proximity switches would provide a data signal to indicate the type of components being used. Such a data signal may also provide to the PAP device 10 the appropriate flow characteristics for the component connected together with the data signal to allow use of the dormant operating mode.

Alternatively, other forms of connector or component recognition may be used as discussed in ResMed's U.S. provisional application No. 60/656,880 filed 1 Mar. 2005, the entirety incorporated herein by reference. For example, the patient interface system may comprise a radio frequency identification (RFID) tag that provides a data signal 32 to the mode control system 34 present in the PAP device 10. In this embodiment, the mode control system 34 present in the PAP device 10 is a RFID scanner that detects the data signal 32 and activates the dormant operating mode.

1.4 Dormant Operating Mode

The at least one dormant operating mode present within the PAP device 10 may include any known PAP operating mode, for example, an automatic adjusting (AutoSet®) mode, Bilevel mode, an automatic Bilevel mode and/or an Expiratory Pressure Relief type operating mode. There may be a series of different data signals, such as electronic chips or smart cards, that each activates a different dormant operating mode present within the PAP device 10.

As noted above, the dormant operating mode may be an automatically adjusting (AutoSet®) operation mode. An AutoSet® mode would provide an enhanced level of comfort to the user of the PAP device as the delivered pressure is commonly lower than those provided by a CPAP device set to deliver the maximum pressure requirement. In an embodiment, the AutoSet® operating mode may be provided using a low cost system that does not require the use of sophisticated sensors, e.g., using the session-by-session adjusting device as described in ResMed's application PCT/AU2005/000174 filed 10 Feb. 2005, the entirety incorporated herein by reference. Alternatively, the PAP device may use the algorithmic flow estimator system described in ResMed's U.S. provisional application Nos. 60/624,951 filed 4 Nov. 2004 and 60/625,878 filed 8 Nov. 2004, the entirety of each being incorporated herein by reference. A similar method is described in WO2004/067070, which is assigned to SAIME S A, the entirety incorporated herein by reference. It is understood that any method of providing an automatically adjusting operation mode or other PAP operation modes are encompassed within the scope of the present invention.

Figure 2:
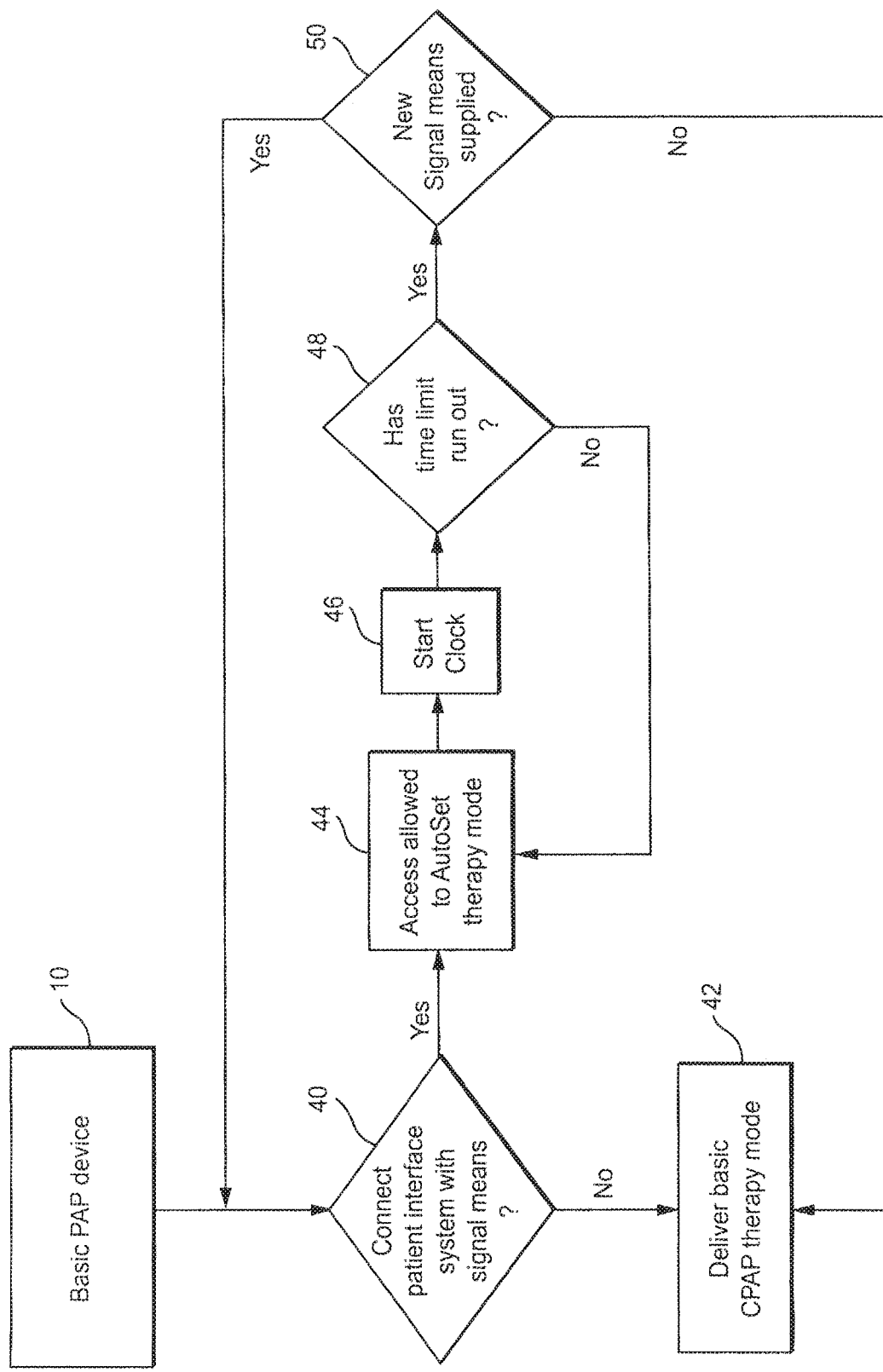
FIG. 2 is a flow diagram showing an overview of an embodiment of the combination enhanced therapy process.

FIG. 2 shows an overview of an embodiment of the combination enhanced therapy process. A basic PAP device 10 is connected to a patient interface system 40. The basic PAP device 10 would provide access to a basic CPAP operating mode 42. However, if the patient interface system comprises a data signal or a separate data signal is provided, then the basic PAP device 10 is enabled to allow access to an AutoSet® therapy mode (dormant operating mode) 44. In the illustrated embodiment, upon access being allowed to the AutoSet® therapy mode 44, a clock would be initiated at 46. The clock 46 may activate the dormant operating mode for a limited time period. In an embodiment, the limited time period would relate to the life of a patient interface system and may, for example, be between three and twelve months, e.g., six months. However, other time periods are encompassed within the scope of the invention.

The limited time period of operation for the activated dormant operating mode may be controlled by starting a clock that counts or monitors a parameter related to time or usage of the activated operating mode. For example, the clock may simply count down or up to a predetermined limit using a calendar type of system. In this regard, the operating mode would only be provided for a set period of time regardless of whether the device was used or not. Alternatively, the clock may allow a predetermined number of hours of use of the activated dormant operating mode, thus the clock would count the numbers of hours of usage and once the limit was reached the activated operating mode would be inactivated again (see FIG. 2). There may also be different data signals that provide different amounts of operating time.

In one embodiment, the PAP device 10 would check whether the time limit set by the data signal had been reached at 48 prior to beginning of each therapy session. Therapy using the AutoSet® therapy mode (dormant operating mode) 44 would only commence if the time limit was below the predetermined limit. If the time limit was equal to or above the predetermined limit, then the PAP device would register the time limit as expired and prevent further access to the dormant operating mode. Thus, only allowing use of the basic CPAP operating mode 42.

Alternatively, the basic PAP device may regularly check the clock throughout the therapy session. If the time limit has not been reached, then access to the AutoSet® therapy mode (dormant operating mode) 44 would be maintained. However, once the time limit is reached, the access to the dormant operating mode would expire and the PAP device would revert to only delivering the basic CPAP operating mode 42.

In a further embodiment, the PAP device would include a 'sleepout' feature that enabled the current therapy session to continue. The 'sleepout' feature would prevent patient discomfort or arousal from sleep due to the dormant operating mode switching to the basic CPAP mode while a patient was sleeping. Thus, if the time limit expires during a therapy session, then the dormant operating mode would not immediately cease, but rather one or more of the following may apply:

a. the device would remain in the activated dormant operating mode until the therapy session ended; or b. the device would remain in the activated dormant operating mode for a further preset time. The duration of that preset time may be fixed (e.g., for five hours) or capable of being adjusted (e.g., be adjustable between the range of 4 to 10 hours). Alternatively, the preset time may be established by reference being made to the average duration of preceding therapy periods. For example, a calculation is made of the average therapy session duration for the preceding (e.g., five) therapy sessions. To avoid calculation of an undesirably low preset time, a default session time may be included to take precedence over an undesirably short preceding therapy session. For example, should a preceding therapy session be of less than five hours duration, then a default period of five hours will be substituted for that session in the calculation of the average. The calculated average would be set as the preset time that would apply for the continuance of the availability of the dormant operating mode only during the session in which the time limit set by the data signal expires.

As illustrated in FIG. 2, the dormant operating mode may be capable of repeated activations by further data signals 50. The further data signals may be provided by purchasing further patient interface systems. The data signal would again allow access to the AutoSet® therapy mode 44 and the process would be repeated. Each further activation of the dormant operating mode by a data signal would initiate a new predetermined time period of operation of the dormant operating mode.

In a further embodiment, the PAP device would inform the user that the system had changed from dormant operating mode to basic CPAP mode. This may be achieved by way of a message appearing on a visual display, an auditory signal and/or communications transmitted by wireless or hardwired networks to a computer. The system may provide a reminder to the user that it is time to replace the patient interface system and/or to obtain a new data signal. In an embodiment, the device may provide a reminder to the user prior to the expiration of the predetermined time limit. The message may also provide instructions to the user on the use of the device and contact details of a clinician or other healthcare professional.

In the default setting, the PAP device would provide basic PAP operating functions. The addition of a data signal, for example present on an electronic chip or card, an RFID tag or pin code, would provide access to enhanced functionality in the form of the dormant operating mode present within the PAP device. The data signal is read by the mode control system, which then allows access to the dormant operating mode. In one embodiment, the mode control system would routinely look at the data signal location, for example, every ten seconds or minute. If a valid data code is detected, then access to the dormant operating mode is enabled or continued. If no data signal is detected or an invalid data code is detected, then the dormant operating mode remains dormant, as access is denied.

In another embodiment, the mode control system may destructively read the data signal and enable access to the dormant operating mode for a predetermined amount of time. Thus, the mode control system may activate a clock that counts the predetermined time for use of the dormant operating mode. Once the predetermined time has expired, the signal may be turned off and the PAP device may revert to default settings of providing basic PAP therapy. In an embodiment, the mode control system may be pre-programmed to recognize a set of data signals. In a further embodiment, the mode control system may be capable of receiving software upgrades to allow further pre-programming to recognize additional data signals.

1.5 Packaging of the Data Signal

The data signal required to activate the dormant operating mode in a PAP device may be packaged with a compatible patient interface system to encourage the purchase of the compatible patient interface systems. The electronic chip, electronic card, pin or code number or any other data signal device may be provided within the patient interface packaging or issued at the time of purchase of the patient interface system. Alternatively, as discussed previously, the data signal is in-built with the patient interface system.

Further aspects of the invention may include the addition of non-therapeutic benefits that may be linked to the continued use of particular types of patient interface systems (i.e., a customer loyalty program). If a patient were to display continuous use of particular types of patient interface systems, then the access to the dormant operating mode therapy may be extended for longer periods of time. For example, after 3 replacement masks, the dormant operating mode may be activated for 8 months instead of 6 months. Alternatively, the continuous use of particular types of patient interface systems may earn "loyalty points" that may be used for discounts on products or services. The quantity of these "loyalty points" may be reported by a coded value appearing on the LCD or via a Smartcard system. This system may also advantageously provide data on the buying patterns of customers, provided each patient interface system style and size was uniquely coded, that may assist in company management and planning. It may also provide sale organizations with some history of the patient interface systems used by a returning customer such that they could identify potential new patient interface systems for the customer to try if a new model or improved version became available.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A Positive Airway Pressure (PAP) device comprising:
a flow generator configured to generate a supply of pressurized air;
a programmable controller configured to:
control operation of the flow generator based on one or more operating modes, at least one of the operating modes being a dormant operating mode; and
provide access to the dormant operating mode based on determining use of a particular type of patient interface system.

2. The PAP device according to claim 1, wherein access to the dormant operating mode is provided based on determining continuous use of the particular type of patient interface system.

3. The PAP device according to claim 1, wherein the dormant operating mode is an automatically adjusting pressure mode.

4. The PAP device according to claim 1, wherein the dormant operating mode is an Expiratory Pressure Relief (EPR) mode.

5. The PAP device according to claim 1, wherein the dormant operating mode is a Continuous Positive Airway Pressure (CPAP) mode.

6. The PAP device according to claim 1, wherein access to the dormant operating mode is provided for a predetermined period of time after determining use of the particular type of patient interface system.

7. The PAP device according to claim 1, wherein access to the dormant operating mode is provided for a predetermined period of time from determining use of the particular type of patient interface system and access to the dormant operating mode is extended based on determining continuous use of the particular type of patient interface system.

8. The PAP device according to claim 1, wherein the programmable controller includes a clock that is activated by a data signal received from the particular type of patient interface system and access to the dormant operation mode is provided for a predetermined period of time determined based on activation of the clock.

9. The PAP device according to claim 1, wherein the dormant operating mode is repeatably activatable by a data signal received from the particular type of patient interface system.

10. The PAP device according to claim 1, wherein use of the particular type of patient interface system is determined based on a data signal provided by the particular type of patient interface system to the programmable controller.

11. The PAP device according to claim 10, wherein the data signal is a pin or code number.

12. The PAP device according to claim 11, wherein the pin or code number includes numbers, letters and/or symbols or any combination thereof.

13. The PAP device according to claim 1, wherein the programmable controller is configured to receive a data signal from the particular type of patient interface system for determining use of the particular type of patient interface system, and wherein the data signal is provided to the programmable controller upon attachment of the particular type of patient interface system to the flow generator.

14. The PAP device according to claim 13, wherein the data signal is a proximity switch included in a connector of the particular type of patient interface.

15. The PAP device according to claim 13, wherein the data signal is provided based on a radio frequency identification (RFID) tag included in the particular type of patient interface system.

16. A method for configuring a Positive Airway Pressure (PAP) device comprising a flow generator configured to generate a supply of pressurized air and a programmable controller configured to control operation of the flow generator, the method comprising:
receiving, by the programmable controller, programming instructions for operating the flow generator in accordance with one or more operating modes, at least one of the operating modes being a dormant therapy delivery mode;
controlling, by the programmable controller, operation of the flow generator based on the one or more operating modes; and
enabling access, by the programmable controller, to the dormant therapy delivery mode based on determining use of a particular type of patient interface system.

17. The method according to claim 16, further comprising providing a mode control system to the PAP device to receive an activation signal, a command, and/or a code to control access to the dormant therapy delivery mode.

18. The method according to claim 17, further comprising receiving the activation signal, the command, and/or the code from the particular type of patient interface system.

19. A Positive Airway Pressure (PAP) device comprising:
a flow generator configured to generate a supply of pressurized air; and
a controller configured to:
control operation of the flow generator based on one or more pre-stored operating modes, one of the pre-stored operating modes being a dormant operating mode;
determine whether a predetermined patient interface system is connected to the PAP device; and
upon determining that the predetermined patient interface system is connected to the PAP device, activate the dormant operating mode to control operation of the flow generator based on the dormant operation mode.

20. The PAP device according to claim 19, wherein the dormant operating mode is activated for a predetermined period of time from determining that the predetermined patient interface system is connected to the PAP device, and the activation of the dormant operating mode is extended upon determining continuous use of the predetermined patient interface system.

* * * * *